United States Patent [19]

Canna

[11] Patent Number: 5,121,752
[45] Date of Patent: Jun. 16, 1992

[54] APPARATUS AND METHOD FOR SELF-OBTAINING PAP SMEARS

[76] Inventor: Cheral J. Canna, 31 Mt. Vernon Ave., Pitman, N.J. 08071

[21] Appl. No.: 652,819

[22] Filed: Nov. 16, 1990

Related U.S. Application Data

[63] Continuation-in-part of Ser. No. 695,213, Jan. 28, 1985, abandoned.

[51] Int. Cl.5 .............................................. A61B 10/00
[52] U.S. Cl. ...................................................... 128/759
[58] Field of Search ............... 128/759, 758, 757, 749, 128/778; 604/55

[56] References Cited

U.S. PATENT DOCUMENTS

| | | | |
|---|---|---|---|
| 2,553,428 | 7/1948 | Sokolik | 128/841 |
| 3,554,185 | 1/1971 | Kohl | 128/757 |
| 3,592,186 | 7/1971 | Oster | 128/757 |
| 3,750,646 | 8/1973 | Patterson | 128/759 |
| 3,811,443 | 5/1974 | Dickinson, III et al. | 604/55 |
| 3,857,384 | 12/1974 | Watson | 128/749 |
| 4,016,865 | 4/1977 | Fredricks | 128/757 |
| 4,043,322 | 8/1977 | Robinson | 128/758 |
| 4,078,656 | 3/1978 | Crane et al. | 128/757 |
| 4,157,709 | 6/1979 | Schuster et al. | 128/759 |
| 4,384,587 | 5/1983 | Milgrom | 128/757 |
| 4,620,548 | 11/1986 | Hasselbrack | 128/758 |
| 4,628,941 | 12/1986 | Kosasky | 128/759 |
| 4,633,886 | 1/1987 | Bucaso, Jr. | 128/749 |

*Primary Examiner*—Max Hindenburg
*Assistant Examiner*—Guy V. Tucker

[57] ABSTRACT

An apparatus and method of obtaining self-administered PAP smears is disclosed which includes a hollow, cylindrical speculum of suitable minimum inside diameter to permit mirror vision therethrough. The speculum is formed with an angled front orifice wherein the front angle between the orifice and the axis of the speculum is particularly designed to easily fit about the cervix. The entire squamocolumnar junction of the uterine cervix is exposed within the front orifice to permit complete wiping, preferably under visual observation through a hand mirror. A hinged, elongated spatula and an angled endocervical sampler are included as part of the test equipment to faciliate the taking of uncontaminated, accurate specimens.

7 Claims, 3 Drawing Sheets

APPARATUS AND METHOD FOR SELF-OBTAINING PAP SMEARS

This application is a continuation-in-part of Ser. No. 695,213, filed Jan. 28, 1985, now abandoned.

BACKGROUND OF THE INVENTION

1. Field of the Invention

This invention relates generally to methods and apparatus for self obtaining cervical cytologic samples for subsequent testing using the Papanicalou test (Pap test) for the early detection of cervical cancer.

2. Discussion of the Prior Art

The PAP test is a method of screening for uterine, cervical, and vaginal cancer. The American Cancer society recommends that for normal women under forty a PAP smear be taken every three years after three consecutive yearly normal PAP smears. Some gynecologists do not feel this is often enough. This invention is designed as an additional PAP test which can be taken in ones home and which can be used yearly in addition to but not in substitution for the regular three year gynecological examination.

The PAP test is traditionally taken by a gynecologist by inserting a speculum into the vagina in a manner to expose the cervix. To accomplish this, the woman must remain in a reclining position. Various types of speculums and numerous cervical scrapers or probes have been developed for this purpose. The cytologic specimens collected are then placed upon microscope slides, or more recently, in liquid fixative for automated reading. They are evaluated for hormonal levels and to determine the presence of cancers, precancers and vaginal infections.

Most of the prior art equipment has been designed for use by gynecologists and is not suitable for self-administration. There have been previous attempts to develop PAP test apparatus that could be self administered. However, those devices have not included endocervical sampling and have not specifically wiped the squamocolumnar junction, the two places where cancers start. Because of these they are regarded as not safe. The need remains to provide an accurate, non-traumatic self-administered apparatus and method for the collection of cervical tissue for cytologic evaluation.

SUMMARY OF THE INVENTION

The present invention relates to the field of PAP tests, and is directed to an improved apparatus and method for obtaining PAP smears.

In accordance with the teachings of the present invention, a hollow, cylindrical speculum of suitable inside diameter to permit sampling is provided. The speculum is formed with an angular front orifice wherein the front angle between the orifice and the axis of the speculum is designed to comfortably accept the cervix from the angle the cervix meets the vagina when the woman is upright. The orifice edge has a rounded bead to avoid cutting the fragile vaginal tissue. Because of the angularity, the orifice can surround the cervix to facilitate its isolation from the impinging vaginal tissue. The cylindrical body holds back the vaginal tissue which presses inward from all directions. The prior art speculums used by gynecologists only isolate the cervix from vaginal tissue above and below it, and remain in place only when the woman is fully reclining, so they cannot be self-administered. By isolating the cervix in the angular orifice of the speculum, the endocervix and the squamocolumnar junction can be wiped with ease by the user without the danger of loosing wiped cells by brushing them against unrestricted vaginal walls, providing a complete specimen. The inside diameter of the speculum is designed to be large enough to enable the user to observe the positioning of the speculum and use of the probes by employing a hand mirror. In this manner, positioning of the speculum orifice about the cervix, and the sampling, can be checking by visual observation. This provides test results that are far superior to any that have heretofore been achieved with prior art self-administered PAP test equipment.

An angled endocervical sampler and an elongated angled spatula are provided as part of the test equipment to facilitate the taking of specimens from the endocervical canal and the cervix respectively.

The angled front orifice of the speculum, together with the ability to permit visual observation through the hollow speculum interior by utilizing a mirror, assures that uncontaminated specimens can thus be taken, even by unskilled persons.

It is an object of the present invention to provide a novel apparatus and method for self-obtaining PAP smears which includes a hollow speculum with a front orifice that is angled to fit about the cervix, the speculum having sufficient internal diameter to facilitate visual observation by mirror to assure correct placement.

It is another object of the present invention to provide a novel apparatus and method for self obtaining PAP smears which comprises a hollow, plastic speculum, the speculum terminating forwardly in a front orifice that is angled at approximately twenty-six degrees from the longitudinal axis of the speculum, and an endocervical sampling tool having a fibrous sampling end, offset from the handle body by a total angle of approximately one hundred twenty degrees, and a handle which when braced against the inside wall of the speculum gives control to the endocervical sampling, the device being suitable to extract a sample from the endocervical canal, and a spatula having a hinged scraper to conform to the various contours of the cervix during scraping, and an angled handle, which when braced against the inside wall of the speculum, gives even pressure and control to the wipe, and.

Other objects and a fuller understanding of the invention will be had by referring to the following description and claims of a preferred embodiment thereof, taken in conjunction with the accompanying drawings, wherein like reference characters refer to similar parts throughout the several views and in which:

DESCRIPTION OF THE PREFERRED EMBODIMENT OF THE INVENTION

Figure 1:
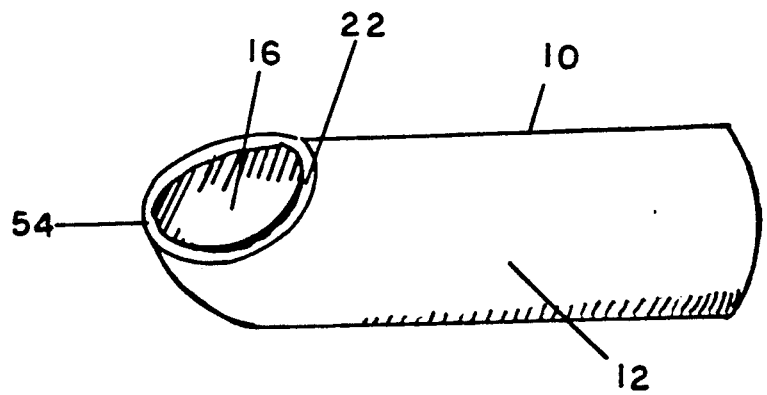
FIG. 1 is a perspective view of a speculum fabricated in accordance with the teachings of the present invention.

Although specific terms are used in the following description for the sake of clarity, these terms are intended to refer only to the particular structure of the invention selected for illustration in the drawings, and are not intended to define or limit the scope of the invention.

Figure 2:
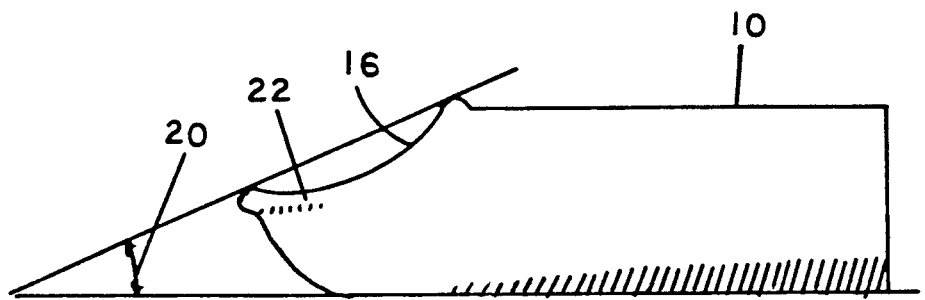
FIG. 2 is a side elevational view of the speculum of FIG. 1.

Referring now to the drawings, there is illustrated in FIG. 1 and 2 a novel speculum 10 which is a hollow cylindrical configuration. Preferably the speculum is fabricated with thick side walls of polypropylene, polyethylene, or other suitable material. The speculum includes a body 12 that is approximately seven inches in length with an enlarged rounded bead 22 about the periphery of the forward orifice. The orifice is designed to minimize injury to the soft vaginal tissue when in use.

The body 12 terminates rearwardly in an unobstructed rearward opening 14 (FIG. 3) and forwardly in an angled orifice 16. As best seen in FIG. 2. The orifice is formed at an angle of between twenty degrees and thirty degrees from a plane drawn parallel to the longitudinal axis of the speculum to facilitate easy application about the cervix 18. An angle of approximately twenty-six degrees has been found to be optimum in most instances for this purpose as indicated by the double headed arrow 20. Preferably, the edge of bead 22 which defines the orifice 16 is rounded as indicated to provide a thickness or diameter of approximately one eighth inch to three sixteenth inches.

Figure 3:
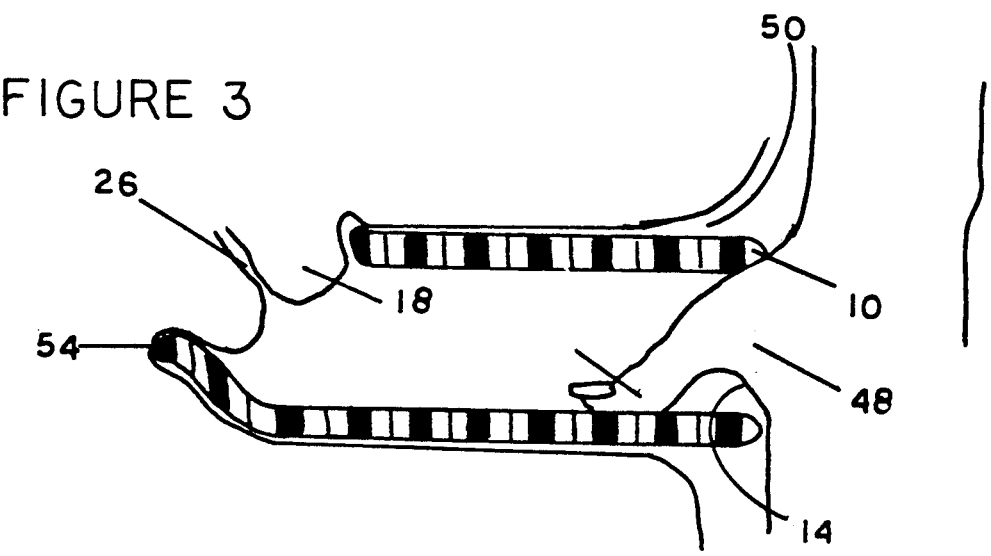
FIG. 3 is a partial cross sectional view showing the speculum being positioned for use.

In order to use the apparatus of the present invention for self-obtaining PAP smears, the speculum 10 should be well lubricated with mineral oil or petroleum jelly (not shown), and then with the users hand 48 positioned as illustrated in FIG. 3, the speculum 10 should be inserted into the vagina 50. The users thumb 52 should be placed interiorly of the rearward speculum opening 14 to permit the speculum to be pressed downwardly during insertion. This downward pressure allows the forward end or or tip 54 of the speculum 10 to pass over the cervix 18 without scraping or other trauma. The speculum should then be manipulated as necessary to position the cervix 18 to reset in the angled orifice 16 comfortably and completely. See FIGS. 3, 5, 7, and 8. When properly positioned, the speculum 10 will have no tendency to back out or to move on its own until the operator consciously moves the speculum. As above set forth, a mirror (not shown) can be employed by the user to visually observe that the bead 22 of the orifice completely surrounds the cervix.

Figure 4:
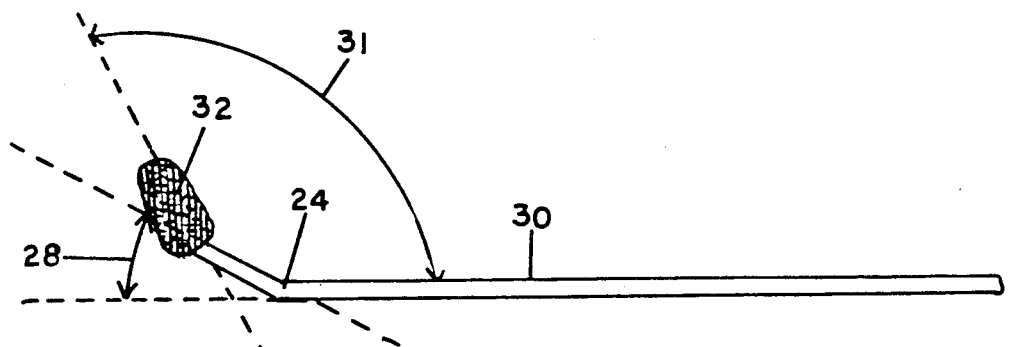
FIG. 4 is a perspective view of the endocervical sampler as used in the present invention.
Figure 5:
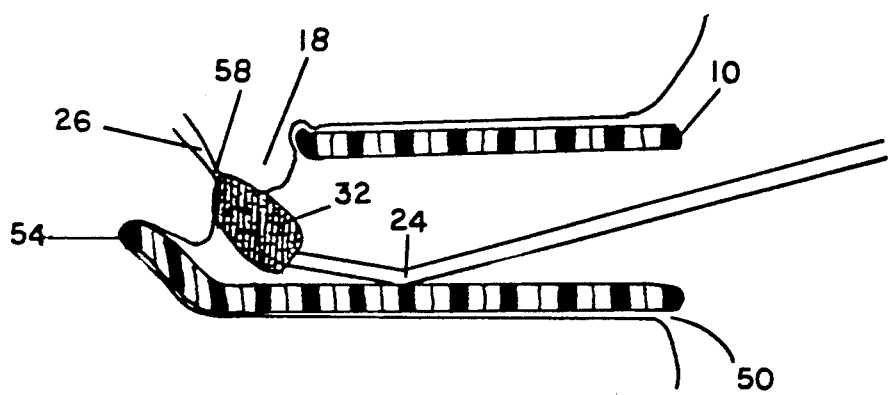
FIG. 5 is a partial cross sectional view similar to FIG. 3 showing the endocervical sampler in use.
Figure 6:
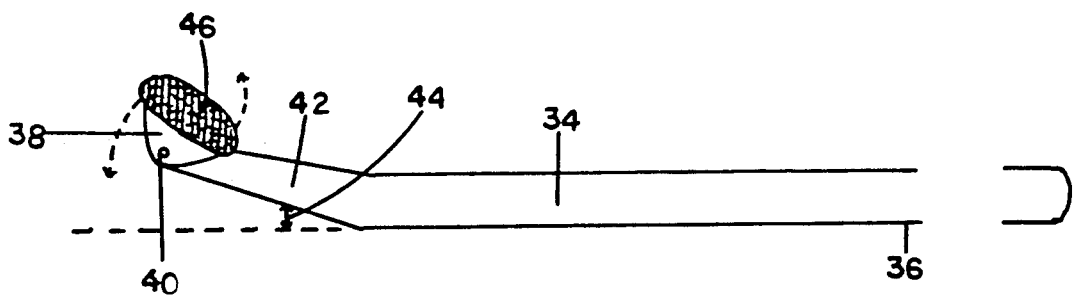
FIG. 6 is a side elevational view of the hinged spatula of the present invention.

Referring now to FIGS. 4 and 5, with the speculum 10 properly positioned, the endocervical sampler 30 can be inserted through the hollow interior 56 of the speculum 10, it's angle 24, approximately 25 degrees, braced against the inside wall of the speculum, and the fibrous tip 32, angled at the angle 31, approximately 117 degrees, inserted into the endocervical canal 26, to remove a portion of the mucoid fluid 58 from the entrance to the endocervical canal. Preferably, a hand mirror (not shown) can be employed to assure the proper positioning of the bent tip 32 directly within the endocervical canal 26. It will only be necessary to enter the opening into the endocervical canal 26 approximately one quarter to one half of an inch to obtain a suitable specimen. The material 58 thus removed when the endocervical sampler is withdrawn through the speculum 10 should then be placed on a conventional slide and covered with a carbowax fixative in well known manner, or placed in a liquid fixative for automated reading.

Figure 7:
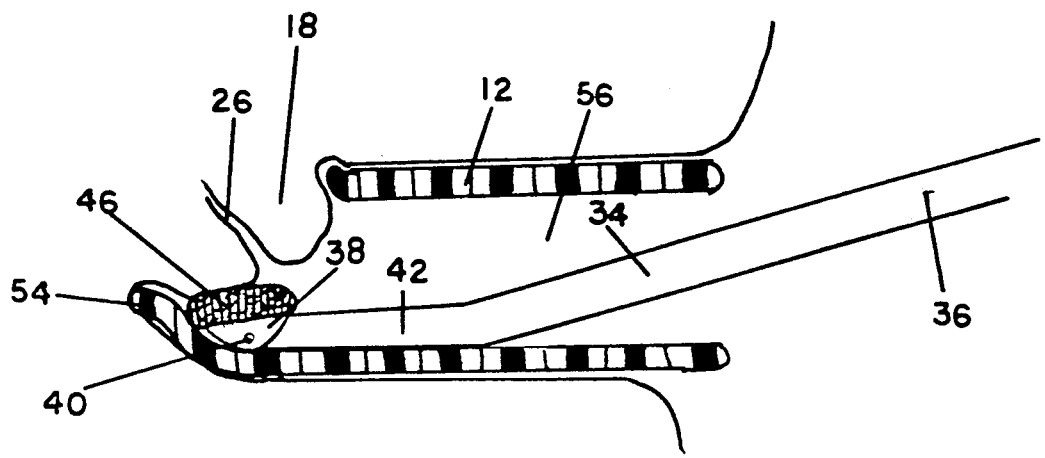
FIG. 7 is a cross sectional view similar to FIG. 5 showing the spatula in use.
Figure 8:
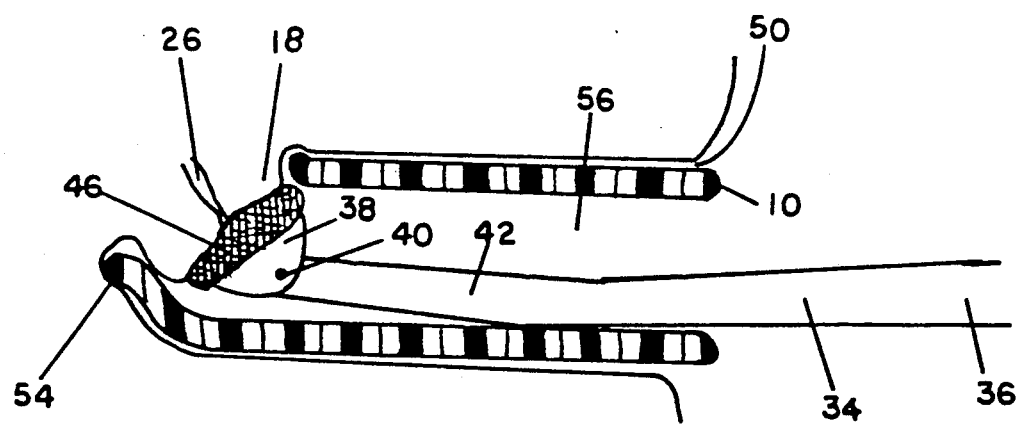
FIG. 8 is a cross sectional view similar to FIG. 7 showing the spatula in use to wipe additional surface areas of the cervix.

Referring now to FIGS. 7 and 8, an elongated spatula 34 is then inserted forwardly through the interior 56 of the speculum 10 until the wiping surface 46 of the hinged scraper head 38 touches the surface of the cervix 18. The operating end 42 of the handle body 36 is offset from the rest of the handle body by an angle of approximately thirteen degrees. By manipulating the handle body 36, and by levering it's angle against the speculum interior for even pressure and control, the scraper head 38 should then gently but firmly be moved up one side of the cervix, across the top and then down the other side in a circular motion. All of the material on the scraper wiping surface 46 (squanmous cell sample) should be deposited on the slide marked "vaginal", or placed in a fluid fixative for automated reading. The spatula should then be re-introduced through the speculum and the procedure should be repeated in the opposite direction to be sure that the entire squamocolumnar junction is wiped. The circular wiping may be repeated if it is felt that any portion of the cervix is missed. Because of the advantages provided by the angular offset of the operating end 42 from the axis of the spatula handle 36, a hand mirror (not shown) may be employed to observe the movement of the scraper head over the cervix to thereby assure complete wiping. The squamous cell sample 66 can be applied upon a glass slide, and covered in known manner with the carbowax fixature or placed in a liquid fixative for automated reading. With the samples properly fixed they can be shipped to an approved testing laboratory for reading.

Although the invention has been described with a certain degree of particularity, it is understood that the present disclosure has been made only by way of example and that numerous changes in the details of construction and the combination and arrangement of parts may be resorted to without departing from the spirit and scope of the invention. Thus the scope of the invention should not be limited by the foregoing specifications, but rather, only by the scope of the claims appended hereto.

What is claimed:

1. An apparatus for self-obtaining PAP smears from the cervix of a woman in an upright position comprising
   a rigid elongated cylindrical speculum having an inside diameter of approximately two inches thereby allowing viewing therethrough and allowing room for sampling, a length defined between a forward terminus adapted to engage and surround the cervix and a rearward terminus, and a longitudinal axis;
   an elongated spatula comprising a handle of length greater than the length of said speculum and a scraper head hingedly connected to the handle by a hinged mechanism allowing only one-directional rotation;
   said scraper head being adapted and sized to facilitate wiping the surface of the cervix;
   said spatula handle comprising a longitudinal body extending most of the length of the handle and an operating end extending the balance of the handle;

said operating end being angularly offset from the longitudinal body by thirteen degrees;

whereby said handle accommodates the user and facilitates leverage against the sides of the speculum, allowing control and pressure to be applied to said scraper head.

2. The apparatus of claim 1 wherein said angled orifice is finished by a dulled edge defining a rounded bead to avoid cutting the delicate vaginal tissue.

3. The apparatus of claim 1 wherein said angled orifice is angled at approximately 26 degrees with respect to the longitudinal axis of the speculum.

4. The apparatus of claim 1 further comprising an endocervical sampler insertable through the speculum body and adapted to contact a central position of the cervix.

5. The apparatus of claim 4 wherein said endocervical sampler comprises an elongated handle of length greater than the length of the speculum and a narrow fibrous sampling tip offset from the handle body.

6. The apparatus of claim 5 wherein said fibrous sampling tip is offset at an angle of approximately 117 degrees from the longitudinal axis of the handle.

7. A method for self-obtaining PAP smears from the squamocolumnar junction of the uterine cervix and from the endocervical canal of an upright woman comprising the steps of inserting a rigid hollow speculum having an angle orifice into the user's vagina;

manipulating the speculum and positioning the speculum so that the cervix to rests in the angled orifice;

inserting an angled endocervical sampler through the speculum and entering the endocervical canal to obtain a tissue sample from the canal for a smear;

inserting an elongated angled spatula with a hingedly mounted scraper head through the speculum and wiping the squamocolumnar junction to obtain tissue for a second member.

* * * * *